United States Patent [19]

Berrehail

[11] Patent Number: 4,550,724
[45] Date of Patent: Nov. 5, 1985

[54] ORTHOPEDIC VEST FOR SUPPORT AND RESTRAINMENT IN THE TREATMENT OF SUBJECTS TO TRAUMA AND SURGERY OF THE SHOULDER, SCAPULAR ARCH AND UPPER LIMB

[76] Inventor: Mohamed Berrehail, Immeuble Royal, Les Doux-Alpes (Isere), France

[21] Appl. No.: 456,020
[22] PCT Filed: Apr. 14, 1982
[86] PCT No.: PCT/FR82/00071
 § 371 Date: Dec. 28, 1982
 § 102(e) Date: Dec. 28, 1982
[87] PCT Pub. No.: WO82/03767
 PCT Pub. Date: Nov. 11, 1982

[30] Foreign Application Priority Data

Apr. 28, 1981 [FR] France ............... 81 08625
Dec. 14, 1981 [FR] France ............... 81 23781

[51] Int. Cl.⁴ ............... A61F 13/00; A61F 5/40
[52] U.S. Cl. ............... 128/133; 128/94; 128/165; 128/134
[58] Field of Search ............... 128/82, 85, 94, 133, 128/134, 165, DIG. 19

[56] References Cited

U.S. PATENT DOCUMENTS 2,549,703 4/1951 Neu ............... 128/94
2,943,859 7/1960 Koski et al. ............... 128/165
3,245,405 4/1966 Gardner ............... 128/165
3,315,671 4/1967 Creelman ............... 128/134
3,559,640 2/1971 Beckett ............... 128/94
3,780,729 12/1973 Garnett ............... 128/94
3,854,156 12/1974 Williams ............... 128/134
3,920,012 11/1975 Patel ............... 128/134

Primary Examiner—Gene Mancene
Assistant Examiner—C. W. Shedd
Attorney, Agent, or Firm—Karl F. Ross; Herbert Dubno

[57] ABSTRACT

Support and restraint of the shoulder, scapular arch, and upper arm limb is provided by an orthopedic vest formed by three panels which are joined, including a first panel having a back portion for the restraint of the rear portion of the thorax, and which extends laterally to a chest portion for the restraint of the front portion of the thorax, shoulder, and upper arm limb, the chest portion extending laterally to a second panel for the restraint of the rear part of the shoulder and upper arm limb, and for receiving at least one part of the first panel and keeping same in place, the chest portion being extended over a lower portion thereof by a third panel forming with the chest portion a rest for the forearm, the panels being provided on both faces thereof with closing and fastening means allowing the vest to be used on the left side and right side of the wearer by simple reversal thereof, the first and second panels acting to enclose the shoulder and upper arm limb and being further provided with an opening formed in a lower portion of the first and second panels for the passage of the forearm.

19 Claims, 12 Drawing Figures

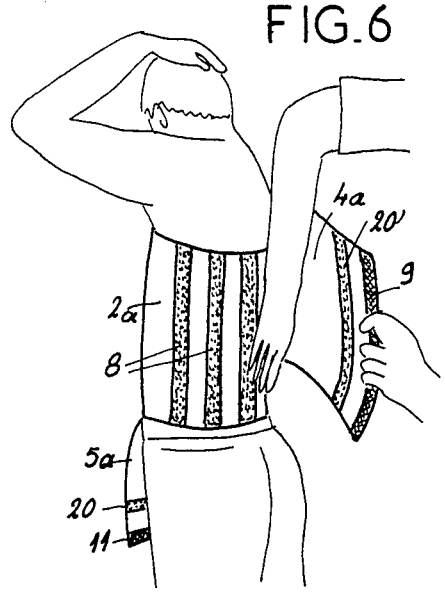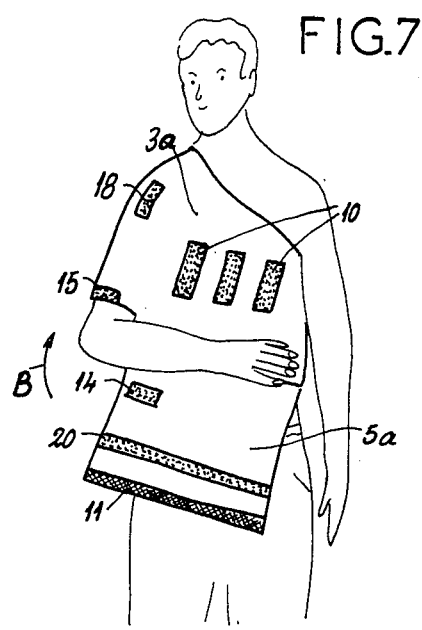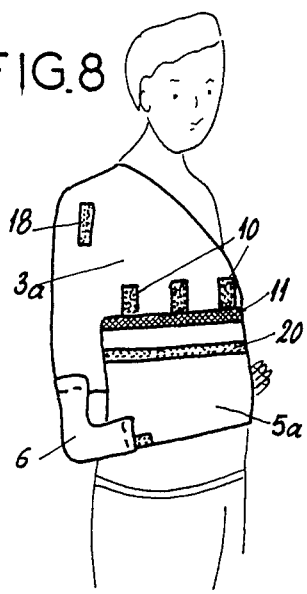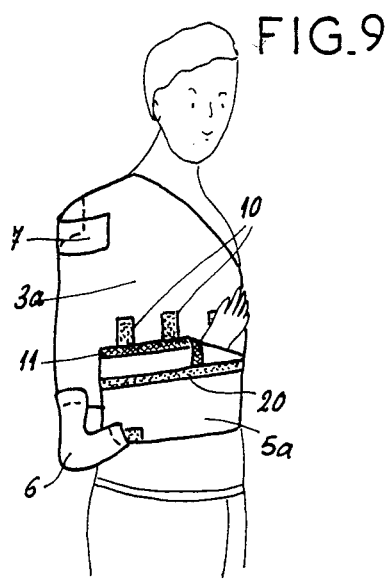

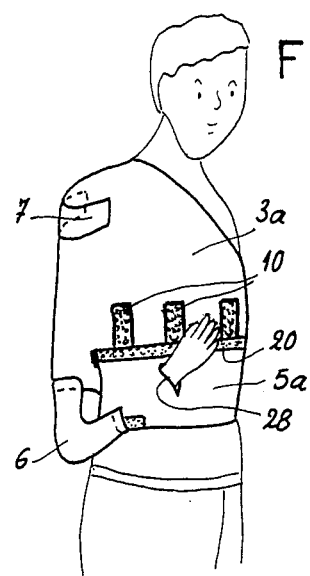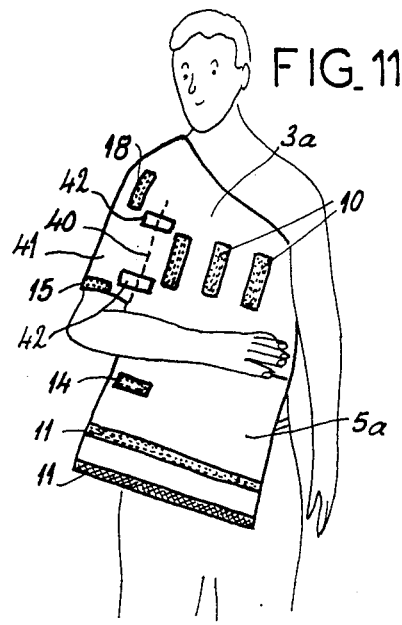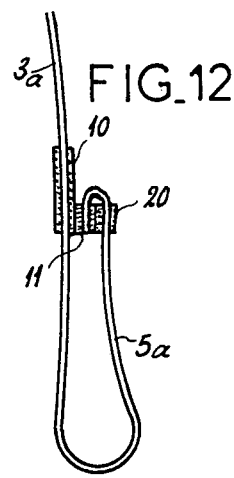

ORTHOPEDIC VEST FOR SUPPORT AND RESTRAINMENT IN THE TREATMENT OF SUBJECTS TO TRAUMA AND SURGERY OF THE SHOULDER, SCAPULAR ARCH AND UPPER LIMB

FIELD OF THE INVENTION

The present invention relates to an orthopedic vest for support and restrainment in the treatment of subjects to trauma and surgery of the shoulder, scapular arch and upper limb.

BACKGROUND OF THE INVENTION

Numerous devices aimed at achieving the support and restrainment of this upper part of the body have already been proposed. Most frequently they are bandages having multiple disadvantages, either related to a frequent lack of strength and resistance of the bandage itself, or to difficulties in maintaining it, resulting in the necessity to frequently redo it. When these bandagess are meant to be used only once their cost is high. At the same time there have been reactions of intolerance by the skin in the case when certain adhesive systems have been used, these bandages do not generally afford comfort to the patient because it is not possible to conveniently provide hygiene or the necessary. local care without undoing or destroying the bandages. Finally, the elbow which often is not affected by the trauma or the surgery, finds itself frequently blocked by the bandage and becomes the location of thereto unrelated pains and sometimes intolerable ankylosis.

OBJECTS OF THE INVENTION

It is an object of the present invention to provde an improved means to alleviate these inconveniences by proposing an orthopedic vest allowing a comfortable and adjustable immobilization and restrainment of the shoulder, scapular arch and upper arm limb of the subjects of trauma and surgery. It is another object to provide an orthopedic means which can be easily applied and removed at any moment to allow a local sporadic intervention for personal hygiene, dressing of wounds, ablation of the stitches, and application of a local treatment.

SUMMARY OF THE INVENTION

According to the invention, the orthopedic vest consists essentially of three joined panels, the first one having a basic portion to restrain the rear portion of the thorax, and extending laterally to a chest portion for the restrainment of the front portion of the thorax, shoulder and upper arm, limb which in turn, extends itself laterally to a second panel for the restrainment of the rear part of the shoulder and upper arm limb and for receiving at least one part of the first panel and keeping it in place, the chest portion being extended over one portion of its lower side by a third panel meant to serve as a rest for the forearm, the panels being provided on both faces with closing and progressive fastening means, permitting the vest to be used with no difference on the left and on the right by simply reversing it.

In accordance with a preferred embodiment of the invention, the first panel is substantially rectangular and is extended laterally by on its lower side by a substsantially horizontal line extending the length of the lower side of the first panel, its upper part being formed with an ascendantly concave curve and at the side opposite to the back portion with a descendantly convex curve prolonged with a substantially vertical line, the first panel being joined at this location, by sewing or any other suitable means, to the second panel whose assembly edge has the same profile, the second panel being in addition bordered at its upper side by an oblique line and at its lower side by a substantially horizontal line which extends from the lower edge of the first panel and on its unattached side by a substantially vertical line; the third panel is of substantially rectangular shape and joined at one of its larger sides with the lower part of the chest portion.

In accordance with one of the embodiments of the invention the joining line between the first and the second panel is interrupted at its lower part by a split being provided in the adjoining panels to allow the passage of the forearm.

According to another embodiment, the joining line between the first and the second panel is temporarily interrupted and an opposed indentation is provided on both sides of this interruption, in the adjoining panels allowing the creation of an opening permitting the passage of the forearm. The two panels forming the body of the vest can be extended down to the waist of the wearer; the third panel serving as a rest for the forearm is then joined to the chest portion at the level of a slit provided therein a little above the waist and the rest can be inserted through the slit from one side of the vest to the other contributing to its reversibility. The lower part of the first two panels further comprises advantageously means for affixing to the trousers or the belt of the wearer.

In accordance with another embodiment, the two panels end above the waist of the wearer and the third panel is joined to the first at the level of its lower edge. The different panels constituting the body of the vest are made of a material which permits the panels to exercise by themselves a certain restrainment of the wearer.

According to a feature of the invention, this material is a fabric or elastic knit.

According to another feature of the invention the material of which the body of the vest is made consists of an ensemble of waterproof layers, sealedly joined together, and the different panels can be inflated by the introduction of any fluid especially air. The different panels can also be inflated by a system of depression usually known as shell-mattress.

In accordance with the invention it also seemed interesting to improve the vest by equipping it with means both to protect the elbow of the patient and to keep the forearm in place, and to prevent it from sliding out of the vest, as well as with means permitting the exercise a more or less strong backwards traction of the shoulder at will and to keep the shoulder in position of external rotation.

According to a preferred embodiment of the invention the vest is equipped with a small removable or semi-removable tongue provided with means of attachment to cooperate with other means placed on the vest in order to ensure the protection of the elbow and the keeping of the forearm within the vest, another removable small tongue being located at the level of the shoulder where it is kept by proper means of attachment and allowing to exercise at will a more or less strong backwards traction of the shoulder and, to keep the shoulder in postion of external rotation by adjustable fastening means provided on the vest cooperating with the attachment means of the small tongue.

The small tongues are preferably made of an elastic material, possibly having the same nature and composition as the material used to make the body of the vest.

BRIEF DESCRIPTION OF THE DRAWING

The present invention will be in fact better understood and its advantages will be better defined by the following description with reference to the drawing, in which:

FIGS. 4 to 11 represent different steps of donning and fastening into place the vest represented in FIG. 1; and FIG. 12 is a cross-sectional view through the armrest thereof.

SPECIFIC DESCRIPTION

Figure 1:
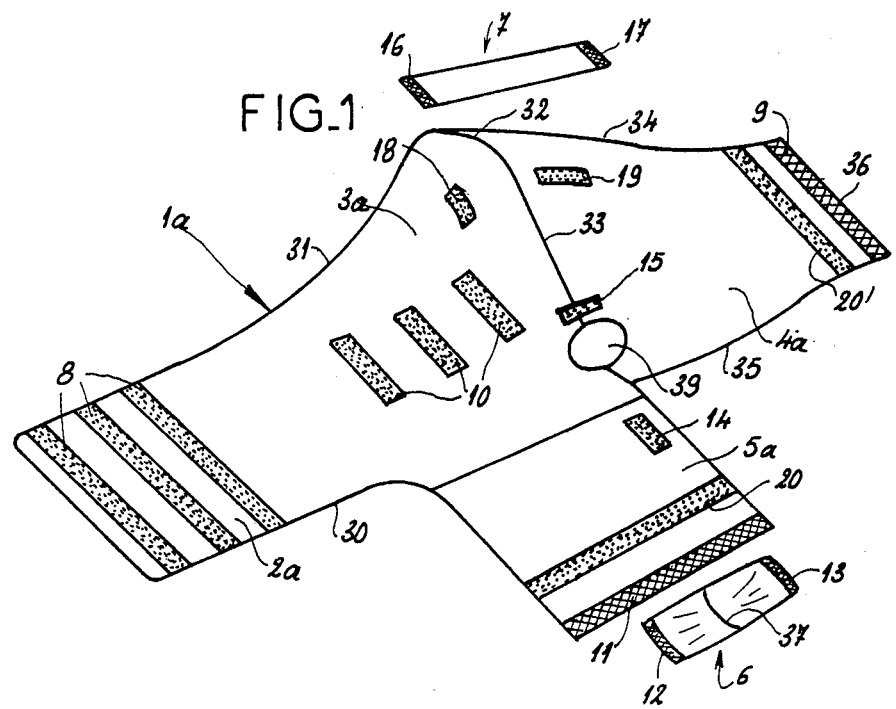
FIGS. 1, 2 and 3 are perspective views of different embodiments of the vest according to the invention.

In FIG. 1 the first, second, and third panels constituting the vest are respectively marked 1a, 4a and 5, the panel 1a being formed by back portion 2 and chest portion 3, the small tongue 6 provided to ensure the protection of the elbow and the holding of the forearm, and the small tongue 7 is provided to exercise a traction on the shoulder and thereafter to hold the latter in a desired position.

The different panels and the two small tongues are provided with respective fastening means 8, 9, 10, 11, 12, 13, 14, 15, 16, 17, 18, and 19, ensuring by mutual engagement their attachment, tightening and stability.

As shown in FIG. 1 the vest according to the invention consists mainly of three joined panels 1a, 4a and 5a.

The back portion 2a is substantially rectangular and is laterally extended by the chest portion 3a, limited on its lower side by a substantially horizontal edge 30, extending the length of the lower edge of the panel 1a it is equally limited at its upper part by a ascendantly concave curve 31 and on the side opposite to portion 2a by a descendantly convex curve 32 extended by a substantially vertical line 33; the panel 1a is joined beginning at the curve 32 and continuing along line 33, joined to the panel 1a. This joining can be effected by sewing, by fusion or by any other convenient method according to the nature of the material the vest is made of. The panel 4a whose assembling edge has the same profile as the the edge of the panel 1a to which it is joined, is limited at its upper part by an oblique edge 34 and at its lower part by a substantially horizontal edge 35 prolonging the lower edge of panel 1a. It is limited at its unattached side by a substantially vertical edge 36. The panel 5a meant to serve as a rest for the arm has a substantially rectangular shape and is joined by one of its larger sides to the lower part of the chest portion 3a. The small tongue 6 provided to ensure the protection of the elbow and the holding of the forearm is essentially rectangular. It is advantageously curved at 37 in order to allow the tongue to better follow the shape of the elbow.

The small tongue 7 provided to exercise a traction on the shoulder and then to hold it in a desired position is also rectangular.

Figure 3:
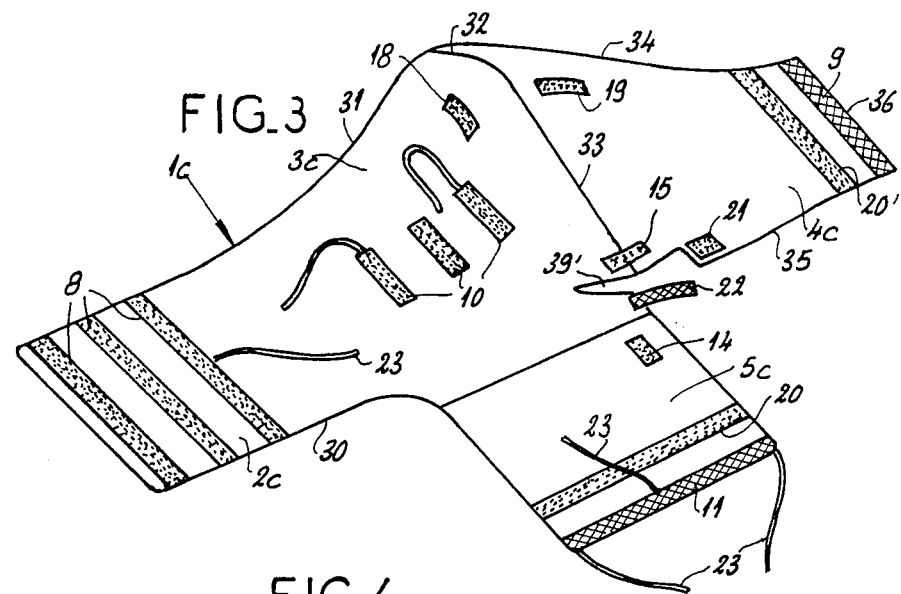

In the embodiment represented in FIGS. 1 and 3, the vest as a whole is designed to stop above the waist and the rest 5a and 5c joined to the portion 3a and 3c at the level of their lower edge.

Figure 2:
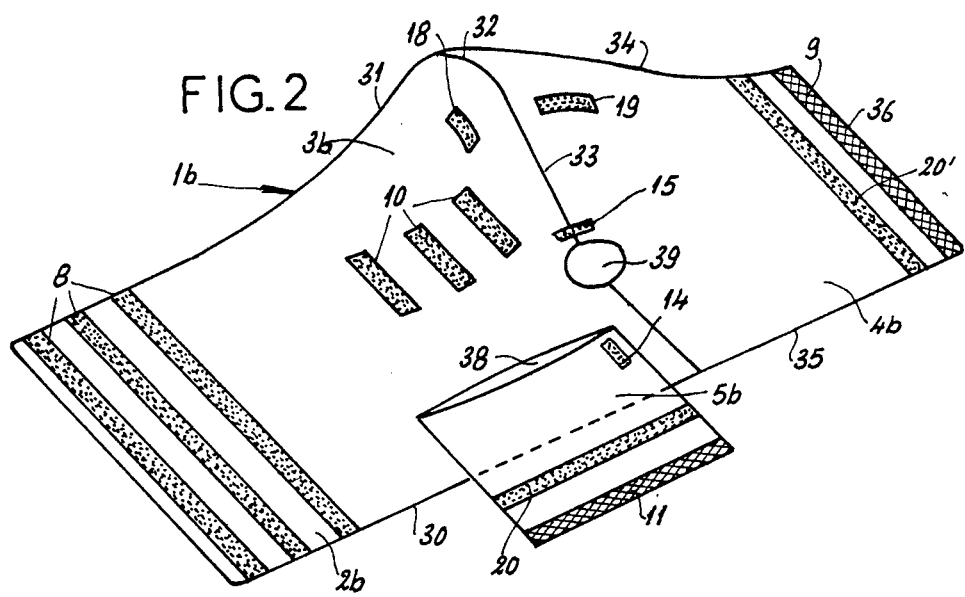

In the embodiment represented in FIG. 2 the panels 1b, 4b and 5b forming the body of the vent extend down to the waist and a slit 38 is provided in the portion 3b to allow the passage of the rests 5b joined to the portion 3b to one or the other side of the vest, corresponding to its use on the left or on the right of the wearer. Attachment means (not shown in the drawing) can be provided on the lower part of the panels 1b, 4b and 5b to cooperate with complimentary means provided on the trousers or belt of the wearer.

In the embodiment represented in FIGS. 1 and 2, the joining line between the panels 1a and 1b and 4a and 4b is temporarily interrupted at the elbow level and an indentation cutout 39 is provided on each side to allow the passage of the arm.

In the embodiment represented in FIG. 3, the panels 1c and 4c are joined only to the level of the elbow where a slit-type opening 39' is formed and complementary fastening means 21 and 22 are provided to join the panels 1c and 4c below the level of the elbow.

The diferent steps of donning and fastening in place of the vest now be described in detail.

Figure 4:
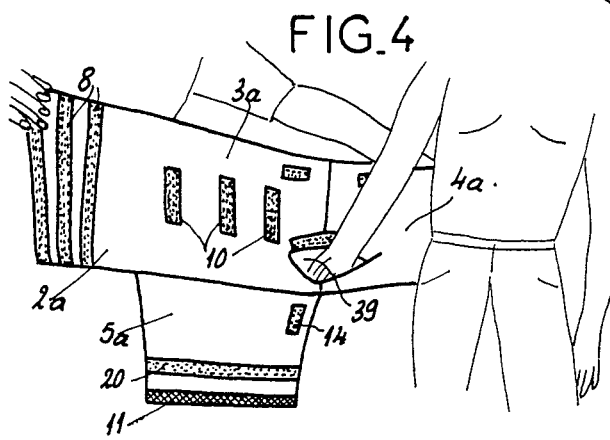

As seen in FIG. 4, the vest is donned like an ordinary vest passing the forearm through the opening 39 provided for this purpose.

In the case of the vest corresponding to the embodiment shown in FIG. 3 the fastening in place will be even more facilitated because in this case it is sufficient to cover the shoulder involved with the unfolded body of the vest and after that, without having to move the arm or the wounded shoulder, to ensure its fastening below the elbow level by the attachment and fixation means 21 and 22; in this embodiment, especially designed for emergency aid, additional fixation means, which can be laces generally marked 23 are also provided to facilitate the donning of the vest at the location of the accident.

Figure 5:
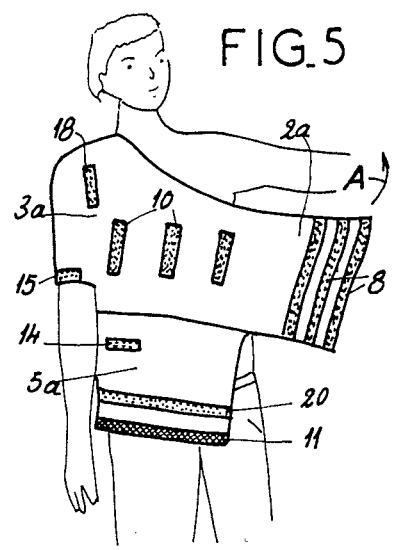

Once the vest is donned, the involved area (shoulder, the collar bone and the omoplate) is wrapped (FIG. 5) and then, as indicated by arrow A the body of the vest is closed at the level of the opposed back and chest region by cooperation of the attachment means 8 and 9. These adjustable means as well as the elastic nature of the material of the body of the vest allow a good molding to the thorax of the patient and ensure a more or less firm containment and immobilization (FIG. 6).

In a third step, shown in FIG. 7, the rest 5a is raised as indicated by arrow B and affixed to the body of the vest by cooperation of the adjustable attachment means 10 and 11, the forearm of the patient being preferably bent at an angble of approximately 90°.

Two different positions of the forearm are shown in FIGS. 8, 9 and 10.

In FIG. 10, a slit 28 is provided in the rest 5a to allow the hand to protrude. At this stage and if the condition of the patient requires, it is possible to intercalate a pad of foam or cotton under the forearm or the arm. Further, the protection of the elbow and the holding in place of the forearm is ensured by positioning the small tongue 6 against the elbow and securing it by the cooperation of the means 12 and 13 with the means 14 and 15 respectively located on the small tongue 6, the rest 5a and the body of the vest (FIG. 8). The small tongue 6 is preferably made of an elastic material having the same nature as the material of the body of the vest and the rest 5a. As mentioned before, this small tongue 6 is advantageously curved to better follow the shape of the elbow which it supports with its lower portion. The small tongue 6 can also be permanently affixed at one of its ends either to the rest 5a or to the body of the vest. Finally, as shown in FIG. 9 the small tongue 7 is fastened in place by cooperation of the means 16 and 17 located on the small tongue with the means 18 and 19 provided on both sides of the body of the vest. This way it is possible, especially due to the transversal position of means 19 to exercise a more or less strong backwards traction of the shoulder and then to keep the shoulder in position of external rotation. This small tongue 7 is also preferably made of an elastic material possibly similar to the one the body of the vest and the rest 5a are made of.

The various means of attachment and fastening 8, 9, 10, 11, 14, 15, 18 and 19 are arranged on the two faces of the body of the vest and of the rest 5a thus creating the possibility to obtain in a simple way a reversible vest, allowing for use on the left or on the right by simply reversing it. These fastening means, as well as the fastening means 12, 13, 16 and 17 arranged on the small tongues can be of any known type capable to cooperate and possibly of the hook and eye type as the ones known in commerce under the trademark of VELCRO.

Advantageously it is possible to provide in this case a supplementary fastening means like the one represented in a general manner at 20 on rest 5a and 20' on panel 4a, in order to cooperate with one of the fastening means 11, thus preventing any uncomfortable roughness on the inside of the rest 5a or the body of the vest (FIG. 12).

In the embodiment represented in FIG., 11 an external or internal sleeve system 41 is provided for instance, with the aid of a seem 40 to facilitate the protection of the thorax region and to contribute to the comfort of the wearer. This sleeve system is evidently also equipped with its own system of reversibility 42. Finally, several fastening strips 11 can be provided on the rest 5a in order to adjust the rest to the shape of the arm to be supported.

The orthopedic vest according to the invention thus constitutes a new means of immobilization and restrainment of the upper limb, the shoulder and the scapular arch. Its reversibility and extensibility allow for its use at will on the left or on the right and for its adjustment to all configurations. In emergency traumatology it can be used as a splint wrapper.

As is self-understood and can be concluded from the preceding, the present invention does not limit itself only to the embodiments described; on the contrary, it comprises all the alternatives, more particularly whatever may be the nature and material constituting the body of the vest.

I claim:

1. An orthopedic vest for support and restraint of the shoulder, the scapular arch and the upper arm limb, comprising: three joined panels including a first panel having a back portion for restraint of the rear portion of the thorax, and extending laterally to a chest portion for the restraint of the front portion of the thorax, the front part of the shoulder, and the upper arm limb, said chest portion extending laterally to a second panel for the restraint of the rear part of the shoulder and the upper arm limb and for receiving at least one part of said first panel and keeping same in place, said chest portion being extended over a lower portion thereof by a third panel forming with said chest portion a rest for the forearm, said panels being provided on both faces thereof with closing and progressive fastening means allowing the vest to be used without difference on the left side and on the right side of the wearer by simple reversal thereof, said first and second panels acting to enclose the shoulder and upper arm limb and being further provided with an opening formed in a lower portion of said first and second panels for the passage of the forearm.

2. The orthopedic vest defined in claim 1 wherein the back portion is substantially rectangular and is extended laterally by the chest portion, said chest portion being formed at its lower side by a substantially horizontal line extending from the lower side of the back portion, and at the upper part with an ascendently concave curve and on the side opposite to the back portion with a descendantly convex curve prolonged with a substantially vertical line, said back portion being joined at this location to the second panel having an assembling edge formed with the same profile, said second panel being further formed at the upper side thereof by an oblique edge, and at the lower part thereof by a substantially horizontal edge which extends along the lower edge of the back and chest portions and on the unattached side thereof by a substantially vertical edge, the third panel being of substantially rectangular shape and joined by one of the larger side thereof with the lower part of the chest portion.

3. The orthopedic vest defined in claim 2 wherein the joining line between the first and second panel is interrupted at its lower part and formed thereat with a split in said first and second panels allowing for the passage of the forearm.

4. The orthopedic vest defined in claim 2 wherein the joining line between the first and second panel is temporarily interrupted by opposed indentations provided on both sides of the interruption formed in said first and second panels for allowing the creation of the opening permitting the passage of the forearm.

5. The orthopedic vest defined in claim 2 wherein the first and second panels forming the body of the vest extend down to the waist of the wearer and the third panel is joined to the first panel at the level of a slit provided in said chest portion above the waist.

6. The orthopedic vest according to claim 5 wherein fastening means are provided at the lower parts of the first and second panels to cooperate with complimentary means provided on trousers or belt of a wearer.

7. The orthopedic vest defined in claim 2 wherein a first removable tongue is provided having first fastening means of attachment which cooperates with second fastening means provided on said panels, whereby said first tongue provides support and protection of the lower part of the elbow and the holding of the forearm within the rest.

8. The orthopedic vest defined in claim 7, further comprising a second removable tongue attached at the level of the shoulder and provided with third fastening means allowing exercise at will and providing a strong backward traction of the shoulder while keeping the shoulder in a position of external rotation by adjustable fourth fastening means provided on said vest and capable of cooperating with said third fastening means of said second tongue.

9. The orthopedic vest defined in claim 8 wherein said first and second tongues are made of an elastic material.

10. The orthopedic vest defined in claim 8 wherein complementary means of the hook and eye type are provided on said first and second tongues to cooperate with means of the hook and eye type appearing on the surface of the vest.

11. The orthopedic vest defined in claim 2 wherein the panels are made of an elastic fabric.

12. The orthopedic vest defined in claim 2 wherein the panels consist of an ensemble of waterproof layers sealedly joined together and which can be inflated by introduction thereon of a fluid.

13. The orthopedic vest defined in claim 2 wherein the closing and fastening means are of the eye and hook type.

14. The orthopedic vest defined in claim 13, further comprising a sleeve system external or internal with respect to the vest, having its own system of reversibility and tightening.

15. The orthopedic vest defined in claim 13 wherein the rest is equipped with several fastening means placed contiguously in a manner to allow adjustment of the rest to the size of the arm to be supported.

16. The orthopedic vest defined in claim 2 wherein the joining line provided between the first and second panels is interrupted at the level of the elbow and an opposed indentation is provided on both sides of said joining line in said first and second panels to allow the passage of the arm.

17. The orthopedic vest defined in claim 2 wherein the first and second panels are joined only to the level of the elbow and complimentary fastening means are provided to join the first and second panels below the level of the elbow.

18. The orthopedic vest defined in claim 2 wherein an opening is provided in the rest to allow the hand to protrude.

19. An orthopedic vest for the support and restraint of the shoulder, the scapular arch, the upper arm limb, and the forearm, comprising:
three joined panels including a first panel having a back portion for restraint of the rear of the thorax and extending laterally to a chest portion for the restraint of the front of the thorax and the front part of the shoulder and upper arm limb, said chest portion extending laterally to a second panel for the restraint of the rear part of the shoulder and upper arm limb and for overlying and holding at least a part of said back portion of said first panel, and a third panel formed along the lower edge of said chest portion of said first panel and forming with said chest portion a rest for the forearm, said panels being provided on both faces with fastening means allowing said vest to be used without difference on the left and right side of the user by simple reversal thereof, the first panel being substantially rectangular and having a lower edge substantially horizontal and an upper edge formed with an ascendently concave curve along the chest portion thereof to a point where said first panel joins said second panel and said upper edge of said first panel forms a line which descends in a convex curve to a substantially vertical line, said second panel having the same profile as said first panel along the joined edge therewith, said line following the outline of the shoulder and upper arm limb of the user and forming a supporting cover therefor, the vertical portion of the joining line being interrupted by oppositely opposed cutouts formed in the first and second panels for the creation of an opening permitting the passage of the forearm.

* * * * *